United States Patent [19]

Molnár et al.

[11] Patent Number: 4,569,914

[45] Date of Patent: Feb. 11, 1986

[54] PROCESS FOR THE STERILE MICROPROPAGATION OF PLANT MATERIAL

[75] Inventors: György Molnár; Péter Tétényi; Éva Dobos; Jenö Bernáth, all of Budapest, Hungary

[73] Assignee: Gyogynoveny Kutato Intezet, Budakalasz, Hungary

[21] Appl. No.: 508,613

[22] Filed: Jun. 28, 1983

[30] Foreign Application Priority Data

Jun. 28, 1982 [HU] Hungary ............................. 2085/82

[51] Int. Cl.$^4$ .......................... C12N 5/00; A10B 79/00
[52] U.S. Cl. ......................................... 435/240; 47/58; 47/DIG. 3
[58] Field of Search ............... 435/240, 1, 948; 47/58, 47/DIG. 3

[56] References Cited
FOREIGN PATENT DOCUMENTS
WO81/03255 11/1981 PCT Int'l Appl. ..................... 47/58

Primary Examiner—Lionel M. Shapiro
Assistant Examiner—Rebecca L. Thompson
Attorney, Agent, or Firm—Young & Thompson

[57] ABSTRACT

The invention relates to a process for the production of propagating material of plants by micropropagation in sterile tissue culture which comprises
(a) planting sterile shoot cuttings of plants in solid nutrient medium in a suitable flask, filling up the flask with a suitable liquid nutrient medium optionally containing a growth regulator and growing the shoots in the submersed system; thereafter
(b) cutting up into pieces the ramified culture thus obtained which contains a number of lateral buds and shoots, rooting the top-end shoots and planting the same after adaptation, and subjecting the cuttings prepared from the lower and middle parts of the shoot cultures to further cultivations according to step (a);

and repeating steps (a) and (b) until the desired number of top-end shoots is reached.

2 Claims, No Drawings

PROCESS FOR THE STERILE MICROPROPAGATION OF PLANT MATERIAL

The invention relates to a process for the production of propagating material of plants by vegetative micropropagation in sterile tissue culture.

It is known that the vegetative propagation of certain plants—particularly of diperennial and perennial plants, shrubs, ornamental plants and indoor plants—has several advantages. Thus growth of the complete plant is more rapid from the rooted shoot than from the sown seeds and the vegetative propagation is simpler too. The main advantage of the method results however in the fact that the descendants obtained from a given individual by vegetative methods can be regarded genetically as a single individual having identical properties. This is of particularly great importance in the case of individuals having valuable properties (e.g. medicinal plants having a high alkaloid content, frost-resistant fruit shrubs having a high yield etc.); the propagation of such individuals yields a uniform stand of outstanding qualities and properties.

According to a conventional garden method of vegetative propagation the top-end shoot or other sprouts of the plant to be propagated are cut off and planted in a pot, greenhouse or in the open air, if desired after rooting in water. In the case of certain plants vegetative descendants can be obtained by division of the root system or the tuber. By using the above procedures however the number of the descendants obtainable from a single individual is rather limited.

For the reasons stated above in the case of valuable plants (such as medicinal plants) practice has switched over to sterile tissue cultures, including organ or particularly shoot cultures. In the course of the above process—also called micropropagation—from the disinfected plant shoot a shoot culture is made by methods known per se and the shoots thus obtained are placed into or onto a nutrient medium solidified with agar-agar, where further growth and ramification take place. The solid nutrient medium may optionally contain a combination of plant hormones selected and tested for the plant species in question. Methods of cultivating plant cells, tissues and organs are described among others in the following reference: "Applied and Fundamental aspects of Plant cell, Tissue and Organ Culture"; edited by Reinert and Bajaj; publisher Springer Verlag, Berlin-Heidelberg-New York, 1977.

The shoots and sprouts obtained are separated, rooted and planted, if desired after adaptation in a greenhouse. According to the above process the number of seedlings obtainable from a single plant can be increased to an advantageous extent, although not in the case of all plant species.

The aim of the present invention is to make the above process more efficient and economically feasible for certain plant species too.

The present invention is based on the following recognitions
if the plant takes up the nutrients not only through its lower pole or the roots formed at this part but also through the whole surface thereof, growth becomes stronger and more favorable;
in the case of root induction the use of a hormone-containing solid nutrient medium might be expedient because it gets into direct contact with the cut surface of the plant. The materials which promote shoot induction and enhance shoot growth are however rather remote from the site where they exhibit their effect. These materials could better exert their activity if they were not absorbed through the roots but would directly contact the shoot.

In order to solve the above two tasks it would be evident to apply plant nutrients dissolved in water (e.g. microelements) onto the surface of the plants by spraying, similarly to foliar fertilization generally used in agriculture. Under the conditions of sterile techniques however spraying can not be accomplished, let alone the fact that the achieved affect would be only temporary.

It has been found in a surprising manner that if the shoot culture cultivated in a solid nutrient medium is completely covered with a liquid nutrient medium, i.e. it is temporarily converted into a submersed culture—the plants do not suffer damage and moreover become more ramified and form more shoots. This recognition is particularly surprising because all parts of overland plants above the roots are adapted to assimilation and respiration when being surrounded with air. Thus it could not be foreseen that the vegetative propagability of shoots cultured as water plants in an aquarium would increase by an order of magnitude.

According to the present invention there is provided a process for the production of propagating material of plants by micropropagation in sterile tissue culture. The process of the present invention comprises
(a) planting sterile shoot cuttings of plants into solid nutrient medium placed in a suitable flask, filling up the flask with a suitable nutrient medium optionally containing a growth regulator and growing the shoots in the said submersed system thereafter
(b) cutting up into pieces the ramified culture thus obtained which contains a number of lateral buds and shoots' rooting the top-end shoots by methods known per se and planting the same after adaptation, and subjecting the cuttings prepared from the lower and middle parts of the shoot cultures to further cultivation according to step (a);
and repeating steps (a) and (b) until the desired number of top-end shoots is reached.

The solid nutrient medium is solidified preferably by using agar-agar. The solid nutrient medium provides the shoot culture with basic nutrients through the vascular bundles. The solid nutrient medium also ensures that the shoots are vertically positioned in accordance with natural conditions.

The liquid nutritive solution serves for the direct supply of the shoot culture with substitute nutrients. Cultures inundated with hormone-free nutritive solution comprising mineral salts, sugar and vitamins form shoots that are 30–100% thicker and/or longer.

To the liquid nutritive solution vegetative hormones may be added too. For this purpose e.g. auxiones, cytokinines and gibberellines can be used. From the group of cytokinines 6benzylamino-purine (6-benzyladenine) proved to be particularly preferable. Under the effect of the growth regulators, a mass of shoots begins to ingrow the submersed culture. The said growth is 100–500% more intensive than if the growth regulator was added to the basic nutrient medium. In a culture inundated with a liquid nutrient medium comprising cytokinines, budding and shooting is observed on the complete surface of the shoots and even on the newly developed shoots.

The part of the submersed culture below the surface of the liquid has a Christmas-tree form, while the top-end shoots grown from the nutrient medium form lateral shoots to a smaller extent or even not at all. The said top-end shoots are cut off and rooted in a manner known per se. The plants cultivated from the said top-end roots are completely normal.

The part of the culture below the surface of the liquid bears a large number of buds and lateral shoots of a different stage of development. In order to obtain further cuttings, this part is cut into pieces under sterile conditions. The cuttings are obtained in a hormone-free solid nutrient medium described above, inundated with a liquid nutritive solution and the process is repeated until the desired top-end shoot number is reached.

It is preferable to illuminate the submersed culture for a longer time than usual or to illuminate the same without interruption. This is presumably due to the fact that beneath the surface of the liquid the conditions of assimilation and respiration of overland plants (light-absorption, the gases are dissolved on water etc.) changed.

Further details of the present invention are to be found in the Examples without limiting the scope of protection to the said Examples which serve merely as illustration.

EXAMPLE 1

Submersed propagation of *Amsonia tabernaemontana* in the presence of growth regulator From plants of the *Amsonia tabernaemontana* collection of the "Research Institute for Medical Plants" a 10-15 year old plant containing 12.26% of tabersonine was selected. From this plant on April 25—30 cm long shoots of 20-leaf stage were cut off. For the sake of easier manageability the shoots were cut into shorter pieces about 10 cm long which were then washed with running tap water for about an hour. The leaves were then cut back to about one-fourth and the shoot pieces thus obtained were disinfected in a 3% sodium hypochlorite solution for 15 minutes with constant shaking. The disinfected material was placed in distilled water, sterilized in an autoclave and kept there for 10 minutes with constant shaking. The latter treatments and the following steps were carried out in a sterile pharmacy inoculating box under aseptic conditions. The shoots were removed from the sterile water and cut in a thermally sterilized Petri dish with a scalpel into 2-3 leaf pieces so that the shoot below the lowest leaf was about 1 cm long. The cuttings thus prepared were planted in 200 ml glass flasks containing 100 ml of modified Murasige-Skoog nutrient medium having the following composition:

| | | |
|---|---|---|
| $NH_4NO_3$ | 1650 | mg/l |
| $KNO_3$ | 1900 | mg/l |
| $CaCl_2.2H_2O$ | 440 | mg/l |
| $MgSO.7H_2O$ | 370 | mg/l |
| $KH_2PO_4$ | 170 | mg/l |
| $Na_2EDTA$ | 37.2 | mg/l |
| $FeSO_4.7H_2O$ | 27.8 | mg/l |
| $H_3BO_3$ | 6.2 | mg/l |
| $MnSO_4.7H_2O$ | 22.3 | mg/l |
| $ZnSO_4.7H_2O$ | 8.6 | mg/l |
| KI | 0.83 | mg/l |
| $Na_2MoO_4.2H_2O$ | 0.25 | mg/l |
| $CuSO_4.5H_2O$ | 0.025 | mg/l |
| $CoCl_2.6H_2O$ | 0.025 | mg/l |
| Saccharose | 30000 | mg/l |
| Agar-agar | 10000 | mg/l |
| Nicotinic acid | 0.5 | mg/l |

-continued

| | | |
|---|---|---|
| Pyridoxide HCl | 0.5 | mg/l |
| Thiamine HCl | 0.1 | mg/l |

T. Murashige, F. Skoog,: A revised medium for rapid growth and bioassays with tobacco tissue cultures. *Physiol. Plantarum* 15, 473-497 (1962).

Upon planting, care should be taken that the cuttings immerse into the nutrient medium as deeply as their lower leaves. The cuttings are cultivated at a temperature of 20°-25° C. by alternating artificial illuminated periods (light intensity 10,000 lux) and dark periods in a sequence of 16 hours and 8 hours, respectively. After a week buds appeared in the axils of the cuttings which sprouted into 10-12 leaf stage (about 7 cm long) shoots within a further 2 weeks.

The said sterile lateral shoots are separated from the cutting and cut into 2-4 leaf pieces. The cuttings thus prepared were planted in a nutrient medium having the above composition so that the cuttings penetrate sufficiently deeply (about 1 cm) into the nutrient medium. (For this purpose the cuttings were cut so that the length of the stem below the lowest leaf of the shoot was at least 1 cm).

Thereafter 50 ml of a liquid nutrient medium having the above composition, but containing no agar-agar and completed with 1 mg per liter of 6-benzylamino-purine were poured onto the cuttings placed in 200 ml glass flasks. The cuttings were kept at 20°-25° C. under constant artificial illumination (8000 lux).

Buds sprouted from all the axils of the cuttings. The said buds reached a length of 5-10 cm within 3 to 4 weeks and showed the main characteristic feature that buds and shoots sprouted from the axils of the newly formed shoots. The strongest shoots even grew from the liquid nutrient medium and consequently on the part of the shoot having been in the air (i.e., above the surface of the liquid) on the axils lateral buds appeared to a smaller extent or not at all. The shoot cultures were then cut to pieces by cutting off the 5-7 leaf stage top-end shoots and cutting the lower and middle parts into pieces bearing 5-10 buds or 2-4 leaves. The top-end leaves were planted in a solid nutrient medium having the above composition where from the cuttings strong roots were grown within 2 weeks and the cuttings could be planted in soil.

The cuttings prepared from the lower and middle parts were also planted in solid nutrient medium having the above compositions. Thereafter a liquid nutrient medium containing 1 mg of 6-benzylamino-purine was poured onto the planted cuttings and the culture was cultivated at 20°-25° C. under constant artificial illumination (8000 lux) for 2-4 weeks. During this period the already existing small shoots and sprouted buds grew further and new shoots appeared both on the old and on the new sprouts. The top-end shoots of the shoot culture were cut into pieces at a suitable stage of development and from these pieces rooted plants could be grown. From the lower and middle parts a mass of shoot material could be obtained by repeating the ramification.

By systematic repetition of the process from one single shoot several million rooted plants could be obtained within a year.

EXAMPLE 2

Submersed propagation of tarragon (*Artemisia dracunculus*) in the absence of a growth regulator From field tarragon plants (*Artemisia dracunculus*) in June shoots were cut off (the length was about 10 cm). The shoots were washed in running tap water for about 2 hours and then disinfected in a 3% sodium hypochlorite solution for about 10 minutes. The shoots removed from the disinfecting solution were placed in sterile distilled water for about 20 minutes whereupon they were cut into 2–4 leaf pieces (length about 3 cm) under aseptic conditions and planted in the nutrient medium according to Example 1. Thereafter the liquid nutrient medium according to Example 1 was poured onto the cuttings.

Under the effect of the liquid nutrient medium containing no growth promoter an intensive growth of the shoot culture began. The rate of growth was about 2–5 times greater than that of the growth shoot cutures cultivated without that addition of a liquid nutrient medium. The cultivation was carried out at 20°–25° C. under constant artificial illumination (8000 lux). The tissue cultures cultivated in 200 ml flasks containing 100 ml nutrient medium overgrew completely the air-space of the flasks. The thickness of the 8–15 cm long shoots amounted to 2–3 mm, they were turgescent and relatively less ramified.

On cutting the tissue cultures into 2–4 leaf pieces they were suitable for rooting and further shoot-formation respectively.

According to the most preferred rooting method the shoot cuttings were planted in a nutrient medium having the same composition as described in Example 1, but containing 1 ml per liter of 2,4-dichloro-phenoxy-acetic acid for 24–96 hours. The shoots were then placed in a nutrient medium containing no growth regulator, about 5–10 roots (length 2–5 cm) grew from each cutting within 2 weeks. For planting purposes the rooted plants were grown without adding further liquid nutrient medium. If shoot formation en masse is desired, liquid nutrient medium is added again. Thus in addition to root formation abundant shoot growth is obtained as well, which enables the production of plants en masse. By systematical repetition of this process about 100,000 rooted plants could be prepared within a year.

EXAMPLE 3

Submersed propagation of Vinca rosea (*Catharanthus roseus*) in the presence of kinetine From *Catharanthus roseus* plants grown in a greenhouse 10–15 cm long lateral shoots were cut off, which were washed with running tap water for 4 hours, disinfected in a 1% sodium hypochlorite solution for 25 minutes and rinsed twice in sterile distilled water for 15 minutes each. The shoot cuttings cut to 2–4 leaves were planted in a solid nutrient medium according to Example 1 and kept at 25°–28° C. Illumination periods (artificial light; intensity 10,000 lux) and dark periods were alternated in a sequence of 16 hours and 8 hours, respectively. The top-end cuttings grew further but generally did not ramify. On the other hand on the cuttings obtained from the lateral shoots generally two lateral shoots sprouted. After 3–4 weeks the lateral shoots formed and the grown top-end shoots were cut in pieces, planted into a solid nutrient medium according to Example 1 in glass flasks and 50 ml of liquid nutrient medium was poured into each flask. The composition of the nutrient medium corresponded to the agar-agar free medium according to Example 1, exept that the solution contained 1 mg per liter of kinetine. The lateral shoots formed in the flasks filled up with the solution with 2–3 times thicker than those obtained in the control culture on a solid nutrient medium without inundation.

The growth of the shoots became proportionally more intensive with the increase of the grafting steps of the shoots obtained. The rooting of the top-end shoots was improved as well. By systematic repetition of this method from one single top-end shoot 100,000 top-end shoots could be obtained within a year.

What we claim is:

1. A process for the production of propagating material of plants by micropropagation in sterile tissue culture, comprising
    (a) planting the lower portions of sterile shoot cuttings of plants in a solid nutrient medium in a flask, providing in the flask a liquid nutrient medium, the liquid medium submerging the upper parts of the shoot cuttings, thereby to establish a submersed propagating system;
    (b) cutting up into pieces the culture thus obtained which contains a number of lateral buds and shoots, rooting the top-end shoots and planting the same, and subjecting the cuttings prepared from the lower and middle parts of the shoot cultures to further cultivation according to step (a); and
    repeating steps (a) and (b) until the desired number of top-end shoots is produced.

2. A process as claimed in claim 1, in which said liquid nutrient medium contains a plant growth regulator.

* * * * *